United States Patent
Mills et al.

(10) Patent No.: US 7,366,561 B2
(45) Date of Patent: Apr. 29, 2008

(54) ROBOTIC TRAJECTORY GUIDE

(75) Inventors: Gerald W. Mills, Palm Bay, FL (US);
Martin Brady, Phoenix, MD (US);
Raghu Raghavan, Baltimore, MD
(US); John David, Malabar, FL (US);
Thomas I. Miller, Palm Bay, FL (US);
Matthew S. Solar, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 515 days.

(21) Appl. No.: 09/825,786

(22) Filed: Apr. 4, 2001

(65) Prior Publication Data

US 2001/0053879 A1 Dec. 20, 2001

Related U.S. Application Data

(60) Provisional application No. 60/195,662, filed on Apr. 7, 2000.

(51) Int. Cl.
*A61B 5/05* (2006.01)

(52) U.S. Cl. ............... 600/417; 600/114; 600/410; 606/130

(58) Field of Classification Search ........... 600/417, 600/114, 410; 606/130
See application file for complete search history.

(56) References Cited

U.S. PATENT DOCUMENTS

| | | | |
|---|---|---|---|
| 1,129,333 A | 2/1915 | Clarke | |
| 1,664,210 A | 3/1928 | Hall | |
| 2,119,649 A | 6/1938 | Roosen | 128/2 |
| 2,135,160 A | 11/1938 | Beehuis | 23/239 |
| 3,055,370 A | 9/1962 | McKinney et al. | 128/303 |
| 3,135,263 A * | 6/1964 | Connelly, Jr. | 606/129 |
| 3,223,087 A | 12/1965 | Vladyka et al. | 128/303.13 |
| 3,273,559 A | 9/1966 | Evans | 128/2 |
| 3,282,152 A | 11/1966 | Myer | 88/24 |

(Continued)

FOREIGN PATENT DOCUMENTS

DE 29612100 9/1996

(Continued)

OTHER PUBLICATIONS

Hirschberg, H., et al., "Image-guided neurosurgery—MR compatible stereoactic equipment", http:www.medinnova.no/English/P51466ster.html, 1 p., (Visited Mar. 29, 2001).

(Continued)

*Primary Examiner*—Brian L. Casler
*Assistant Examiner*—Jacqueline Cheng
(74) *Attorney, Agent, or Firm*—Scott A. Marks

(57) ABSTRACT

A surgical alignment device is shown that is controlled remotely through the use of an actuator, where the actuator in turn controls at least one local adjustment device. The alignment device is suited for neurosurgery, although it is not exclusively limited to neurosurgery. The alignment device includes an insertion guide that is coupled to the local adjustment device, the insertion guide being used to guide a device such as a catheter into a patient. The alignment device may also be coupled to a control module such as a microcomputer that controls the orientation of the insertion guide in response to inputs from the surgeon as to a location of interest within the patient.

17 Claims, 9 Drawing Sheets

U.S. PATENT DOCUMENTS

| | | | |
|---|---|---|---|
| 3,402,710 A | 9/1968 | Paleschuck | 128/1 |
| 3,444,861 A | 5/1969 | Schulte | 128/350 |
| 3,508,552 A | 4/1970 | Hainault | 128/303 |
| 3,672,352 A | 6/1972 | Summers | 128/2 R |
| 3,760,811 A | 9/1973 | Andrew | 128/351 |
| 3,893,449 A * | 7/1975 | Lee et al. | 600/459 |
| 4,040,427 A | 8/1977 | Winnie | 604/180 |
| 4,230,117 A | 10/1980 | Anichkov | 128/303 B |
| 4,341,220 A | 7/1982 | Perry | 128/630 |
| 4,345,606 A | 8/1982 | Littleford | 128/784 |
| 4,355,645 A | 10/1982 | Mitani et al. | 128/777 |
| 4,386,602 A | 6/1983 | Sheldon et al. | 128/4 |
| 4,448,195 A | 5/1984 | LeVeen et al. | 128/344 |
| 4,463,758 A | 8/1984 | Patil et al. | 128/303 B |
| 4,475,550 A | 10/1984 | Bremer et al. | 128/303 B |
| 4,483,344 A * | 11/1984 | Atkov et al. | 600/459 |
| 4,571,750 A | 2/1986 | Barry | 623/258 |
| 4,572,198 A | 2/1986 | Codrington | 128/653 |
| 4,579,120 A | 4/1986 | MacGregor | 600/392 |
| 4,598,708 A | 7/1986 | Beranek | 606/1 |
| 4,608,977 A | 9/1986 | Brown | 128/303 B |
| 4,617,925 A | 10/1986 | Laitinen | 128/303 B |
| 4,618,978 A | 10/1986 | Cosman | 378/164 |
| 4,629,451 A | 12/1986 | Winters et al. | 604/175 |
| 4,638,798 A | 1/1987 | Shelden et al. | 128/303 B |
| 4,660,563 A | 4/1987 | Lees | 128/654 |
| 4,665,928 A | 5/1987 | Linial et al. | 128/782 |
| 4,699,616 A | 10/1987 | Nowak et al. | 604/180 |
| 4,706,665 A | 11/1987 | Gouda | 128/303 B |
| 4,733,661 A | 3/1988 | Palestrant | 128/303 B |
| 4,755,642 A | 7/1988 | Parks | 200/283 |
| 4,791,934 A | 12/1988 | Brunnett | 128/653 |
| 4,793,355 A | 12/1988 | Crum et al. | 128/653 |
| 4,807,620 A | 2/1989 | Strul et al. | 128/303.1 |
| 4,809,694 A | 3/1989 | Ferrara | 128/303 B |
| 4,824,436 A | 4/1989 | Wolinsky | 604/53 |
| 4,826,487 A | 5/1989 | Winter | 604/175 |
| 4,869,247 A | 9/1989 | Howard, III et al. | 128/303.1 |
| 4,883,053 A | 11/1989 | Simon | 606/130 |
| 4,896,673 A | 1/1990 | Rose et al. | 128/660.03 |
| 4,902,129 A | 2/1990 | Siegmund et al. | 356/241 |
| 4,922,924 A | 5/1990 | Gambale et al. | 128/772 |
| 4,955,891 A | 9/1990 | Carol | 606/130 |
| 4,957,481 A | 9/1990 | Gatenby | 604/20 |
| 4,986,280 A | 1/1991 | Marcus et al. | 128/774 |
| 4,986,281 A | 1/1991 | Preves et al. | 128/782 |
| 4,989,608 A | 2/1991 | Ratner | 128/653 A |
| 4,991,579 A | 2/1991 | Allen | 128/653 R |
| 5,006,122 A | 4/1991 | Wyatt et al. | 606/130 |
| 5,024,236 A | 6/1991 | Shapiro | 128/735 |
| 5,027,818 A | 7/1991 | Bova et al. | 128/653 R |
| 5,050,608 A | 9/1991 | Watanabe et al. | 128/653 R |
| 5,052,329 A | 10/1991 | Bennett | 116/209 |
| 5,057,106 A | 10/1991 | Kasevich et al. | 606/33 |
| 5,065,761 A | 11/1991 | Pell | 128/660.03 |
| 5,078,140 A | 1/1992 | Kwoh | 128/653.1 |
| 5,078,142 A | 1/1992 | Siczek et al. | 128/653.1 |
| 5,080,662 A | 1/1992 | Paul | 606/130 |
| 5,087,256 A | 2/1992 | Taylor et al. | 606/28 |
| 5,099,846 A | 3/1992 | Hardy | 128/653.1 |
| 5,102,402 A | 4/1992 | Dror et al. | 604/265 |
| 5,116,345 A | 5/1992 | Jewell et al. | 606/130 |
| 5,120,322 A | 6/1992 | Davis et al. | 604/265 |
| 5,125,888 A | 6/1992 | Howard et al. | 600/12 |
| 5,142,930 A | 9/1992 | Allen et al. | 74/469 |
| 5,143,086 A | 9/1992 | Duret et al. | 128/777 |
| 5,154,179 A | 10/1992 | Ratner | 128/653.4 |
| 5,154,723 A | 10/1992 | Kubota et al. | 606/130 |
| 5,163,430 A | 11/1992 | Carol | 128/653.1 |
| 5,166,875 A | 11/1992 | Machida | 364/413.13 |
| 5,171,217 A | 12/1992 | March et al. | 604/53 |
| 5,174,297 A | 12/1992 | Daikuzono | 128/665 |
| 5,186,174 A | 2/1993 | Schlondorff et al. | 128/653.1 |
| 5,201,742 A | 4/1993 | Hasson | 606/130 |
| 5,207,223 A | 5/1993 | Adler | 128/653.1 |
| 5,207,688 A | 5/1993 | Carol | 606/130 |
| 5,211,165 A | 5/1993 | Dumoulin et al. | 128/653.1 |
| 5,222,499 A | 6/1993 | Allen et al. | 128/653.1 |
| 5,230,338 A | 7/1993 | Allen et al. | 128/653 |
| 5,230,623 A | 7/1993 | Gutherie et al. | 433/72 |
| 5,246,448 A | 9/1993 | Chang | 606/130 |
| 5,257,998 A | 11/1993 | Ota et al. | 606/130 |
| 5,263,956 A | 11/1993 | Nobles | 606/130 |
| 5,269,305 A | 12/1993 | Corol | 128/653.1 |
| 5,279,309 A | 1/1994 | Taylor et al. | 128/782 |
| 5,279,575 A | 1/1994 | Sugarbaker | 604/174 |
| 5,290,266 A | 3/1994 | Rohling et al. | 604/272 |
| 5,291,890 A | 3/1994 | Cline et al. | 128/653.2 |
| 5,300,080 A | 4/1994 | Clayman et al. | 606/130 |
| 5,305,203 A | 4/1994 | Raab | 364/413.13 |
| 5,309,913 A | 5/1994 | Kormos et al. | 128/653.1 |
| 5,330,485 A | 7/1994 | Clayman et al. | 606/130 |
| 5,361,763 A | 11/1994 | Kao et al. | 128/653.2 |
| 5,366,446 A | 11/1994 | Tal et al. | 604/180 |
| 5,375,596 A | 12/1994 | Twiss et al. | 128/653.1 |
| 5,380,302 A | 1/1995 | Orth | 604/523 |
| 5,383,454 A | 1/1995 | Bucholz | 128/653.1 |
| 5,387,220 A | 2/1995 | Pisharodi | 606/130 |
| 5,445,166 A | 8/1995 | Taylor | 128/897 |
| 5,452,720 A | 9/1995 | Smith et al. | 128/653.1 |
| 5,464,446 A | 11/1995 | Dreessen et al. | 607/116 |
| 5,470,307 A | 11/1995 | Lindall | 604/20 |
| 5,474,564 A | 12/1995 | Clayman et al. | 606/130 |
| 5,483,961 A | 1/1996 | Kelly et al. | 128/653.1 |
| 5,494,655 A | 2/1996 | Rocklage et al. | 424/9.36 |
| 5,515,160 A | 5/1996 | Schulz et al. | 356/241 |
| 5,517,990 A | 5/1996 | Kalfas et al. | 128/653.1 |
| 5,528,652 A | 6/1996 | Smith et al. | 378/65 |
| 5,572,999 A | 11/1996 | Funda et al. | 128/653.1 |
| 5,575,798 A | 11/1996 | Koutrouvelis | 606/130 |
| 5,618,288 A | 4/1997 | Calvo | 606/130 |
| 5,622,170 A | 4/1997 | Schultz | 128/653.1 |
| 5,638,819 A | 6/1997 | Manwaring et al. | 128/653.1 |
| 5,647,361 A | 7/1997 | Damadian | 128/683.2 |
| 5,658,272 A | 8/1997 | Hasson | 606/1 |
| 5,667,514 A | 9/1997 | Heller | 606/108 |
| 5,695,501 A | 12/1997 | Carol et al. | 606/130 |
| 5,713,858 A | 2/1998 | Heruth et al. | |
| 5,776,064 A | 7/1998 | Kalfas et al. | 600/414 |
| 5,810,712 A | 9/1998 | Dunn | 600/114 |
| 5,833,627 A | 11/1998 | Shmulewitz et al. | 600/562 |
| 5,843,150 A | 12/1998 | Dressen et al. | 607/116 |
| 5,851,183 A | 12/1998 | Bucholz | 600/425 |
| 5,865,842 A | 2/1999 | Knuth et al. | 607/116 |
| 5,871,445 A | 2/1999 | Bucholz | 600/407 |
| 5,873,822 A | 2/1999 | Ferre et al. | 600/407 |
| 5,891,034 A | 4/1999 | Bucholz | 600/426 |
| 5,891,157 A | 4/1999 | Day et al. | 606/130 |
| 5,927,277 A | 7/1999 | Baudino et al. | 128/642 |
| 5,954,687 A | 9/1999 | Baudino | 604/48 |
| 5,957,934 A * | 9/1999 | Rapoport | 606/130 |
| 5,980,535 A | 11/1999 | Barnett et al. | 606/130 |
| 5,984,930 A | 11/1999 | Maciunas et al. | 606/130 |
| 5,993,463 A * | 11/1999 | Truwit | 606/130 |
| 6,044,304 A | 3/2000 | Baudino | 607/116 |
| 6,058,323 A | 5/2000 | Lemelson | 600/408 |
| 6,071,288 A | 6/2000 | Carol et al. | 606/130 |
| 6,076,008 A | 6/2000 | Bucholz | 600/427 |
| 6,110,182 A | 8/2000 | Mowlai-Ashtiani | 606/130 |
| 6,117,143 A | 9/2000 | Hynes et al. | 606/130 |
| 6,120,465 A | 9/2000 | Guthrie et al. | 600/587 |
| 6,206,890 B1 * | 3/2001 | Truwit | 606/130 |
| 6,236,875 B1 | 5/2001 | Bucholz et al. | 600/407 |
| 6,254,532 B1 | 7/2001 | Paolitto et al. | 600/201 |

| | | | |
|---|---|---|---|
| 6,261,300 B1 | 7/2001 | Carol et al. | 606/130 |
| 6,282,437 B1* | 8/2001 | Franck et al. | 600/429 |
| 6,290,644 B1 | 9/2001 | Green et al. | 600/235 |
| 6,298,262 B1 | 10/2001 | Franck et al. | 600/426 |
| 6,529,765 B1* | 3/2003 | Franck et al. | 600/427 |
| 6,546,279 B1* | 4/2003 | Bova et al. | 600/429 |
| 7,204,840 B2 | 4/2007 | Skakoon et al. | |

FOREIGN PATENT DOCUMENTS

| | | |
|---|---|---|
| DE | 19726141 | 1/1999 |
| DE | 19826078 | 8/1999 |
| DE | 19820808 | 11/1999 |
| EP | 0427358 | 5/1991 |
| EP | 0609085 | 8/1994 |
| EP | 0724865 | 8/1996 |
| EP | 0904741 | 3/1999 |
| WO | WO-88/09151 | 12/1988 |
| WO | WO-97/03609 | 2/1997 |
| WO | WO-97/21380 | 6/1997 |
| WO | WO-97/42870 | 11/1997 |
| WO | WO-98/17191 | 4/1998 |
| WO | WO98/25535 | 6/1998 |
| WO | WO-00/01316 | 1/2000 |
| WO | WO-01/49197 A1 | 7/2001 |

OTHER PUBLICATIONS

*Neurosurgery*, 66, (1996),102-107.

Howard, M., et al., "Magnetic Neurosurgery: Image-Guided, Remote-Controlled Movement of Neurosurgical Implants", *Ch. 26 In: Clinical Neurosurgery; Proceedings of the Congress of Neurological Surgeons*, San Francisco, CA,(1995),382-391.

Howard, M., et al., "Review of Magnetic Neurosurgery Research", *J. Image Guided Surgery*, 1, (Nov. 1995),295-299.

Lawson, M., et al., "Near Real-Time Bi-planar Fuoroscopic Tracking System for the Video Tumor Fighter", *SPIE*, 1445, (1991),265-275.

Leggett, W. B., et al., "Surgical Technology—The Viewing Wand: A New System for Three-Dimensional Computed Tomography-Correlated Intraoperative Localization", *Current Surgery*, (Dec. 1991),pp. 674-678.

Malison, R. T., et al., "Computer-Assisted Coregistration of Multislice SPECT and MR Brain Images by Fixed External Fiducial", *Journal of Computer Assisted Tomography*, 17 (6), (1993),pp. 952-960.

McNeil, R., et al., "Characteristics of an Improved Magnetic-Implant Guidance System", *IEEE Transactions on Biomedical Engineering*, 42 (8), (Aug. 1995),pp. 802-808.

McNeil, R., et al., "Functional Design Features and Initial Performance Characteristics of a Magnetic-Implant Guidance System for Sterotactic Neurosurgery", *IEEE Transactions on Biomedical Engineering*, 42 (8), (Aug. 1995),pp. 793-801.

Meeker, D., et al., "Optimal Realization of Arbitrary Forces in a Magnetic Stereotaxis System", *IEEE Transactions on Magnetics*, 32 (2), (Mar. 1996),pp. 320-328.

Molloy, J., et al., "Experimental Determination of the Force Required for Insertion of a Thermoseed into Deep Brain Tissues", *Annals of Biomedical Engineering*, 18, (1990),pp. 299-313.

Molloy, J., et al., "Thermodynamics of Movable Inductively Heated Seeds for the Tratment of Brain Tumors", *Medical Physics*, 18 (4), (Jul./Aug. 1991),pp. 794-803.

Oliver, L., "Cup-And-Ball Chemopallidectomy Apparatus", (1958),p. 401.

Quate, E., et al., "Goniometric Motion Controller for the Superconducting Coil in A Magnetic Sterotaxis System", *IEEE Transactions on Biomedical Engineering*, 38 (9), (Sep. 1991),pp. 899-905.

Ramos, P., et al., "Electro-Optic Imaging Chain for a Biplanar Fluoroscope for Neurosurgery: Magnetic Field Sensitivity and Contrast Measurements", *Optical Engineering* 32 (7), (Jul. 1993),pp. 1644-1656.

Ramos, P., et al., "Low-Dose, Magnetic Field-Immune, Bi-Planar Fluoroscopy for Neurosurgery", *Proc. SPIE*, 1443 (*Medical Imaging V: Image Physics*), (1991),160-170.

"Fathom Remote Introducer", *Image-Guided Neurologics, Inc.*, CNS Hynes Convention Center,(Oct. 30-Nov. 4, 1999),2 p.

Allison, S., et al., "Microchannel Plate Intensifier Response in Transverse Magnetic Field", *Electronic Letters*, 26, (Jun. 7, 1990),770-771.

Drake, J. M., et al., "The ISG Viewing Wand System", *Neurosurgery*, 34 (6), (Jun. 1994), 1094-1097.

Dyer, P. V., et al., "The ISG Viewing Wand: an application to atlanto-axial cervical surgery using the Le Fort I maxillary osteotomy", *British Journal of Oral and Maxillofacial Surgery*, 33, (1995),pp. 370-374.

Gillies, G., et al., "Magnetic Manipulation Instrumentation for Medical Physics Research", *Review of Scientific Instruments*, 65 (3), Review Article,(Mar. 1994),pp. 533-562.

Grady, M., et al., "Initial Experimental Results of a New Stereotaxic Hyperthermia System", *American College of Surgeons: 1998 Clinical Congress: Surgical Forum*, 39, (1998),507-509.

Grady, M., et al., "Magnetic Stereotaxis System for Neurosurgical Procedures", *Proc. 37th International Instrumentation Symp.*, San Diego, CA,(May 1991),665-675.

Grady, M., et al., "Magnetic Sterotaxis: A Technique to Deliver Sterotactic Hyperthermia", *Neurosurgery*, 27 (6), Technical Note,(Dec. 1990),pp. 1010-1016.

Grady, M., et al., "Nonlinear Magnetic Stereotaxis: Three-Dimensional, in vivo Remote Magnetic Manipulation of a Small Object in Canine Brain", *Medical Physics*, 17 (3), (May/Jun. 1990),pp. 405-415.

Grady, M., et al., "Preliminary Experimental Investigation of in vivo Magnetic Manipulation: Results and Potential Application in Hyperthermia", *Medical Physics*, 16(2), (Mar./Apr. 1989),pp. 263-272.

Hata, N., et al., "Needle Insertion Manipulator for CT- and MR-Guided Stereotactic Neurosurgery", *In: Interventional MR: Techniques and Clinical Experience*, F. Jolesz and I. Young, eds.,99-106 (1998).

Howard, M., et al., "Magnetic Movement of a Brain Thermoceptor", *Neurosurgery*, 24 (3), (1989),pp. 444-448.

Howard, M., et al., "Magnetic Neurosurgery", *Sterotactic and Functional*.

Ramos, P., et al., "Microchannel Plate Image Intensifier Electron Dynamics in Magnetic Field", *Electronics Letters*, 27 (18), (Aug. 29, 1991),pp. 1636-1638.

Ritter, R., et al., "Magnetic Stereotaxis: An Application of Magnetic Control Technology to the Needs of Clinical Medicine", *Proc. of the MAG'95 Industrial Conf. and Exhibition*, Technomic Pub. Co., Lancaster, PA., Allaire. P., ed.,(1995), 186-193.

Ritter, R., et al., "Magnetic Stereotaxis: Computer-Assisted, Image-Guided Remote Movement of Implants in the Brain", *Ch. 26 In: Computer-Integrated Surgery; Technology and Clinical Applications*, MIT Press, Cambridge, MA., Taylor, R., et al., eds., (1996),363-369.

Ritter, R., et al., "Stereotaxie Magnetique: Deplacement D'Implants dans le Cerveau, Assistes par Ordinateur et Guides par Imagerie.", *Innovation et Technologie en Biologie et Medecine*, 13, (1992),437-449.

Sandeman, D. S., et al., "Advances in image-directed neurosurgery: Preliminary experience with the ISG Viewing Wand compared with the Leksell G frame", *British Journal of Neurosurgery*, 8, pp. 529-544, (1994)

Szikora, I., et al., "Endovascular Treatment of Experimental Aneurysms with Liquid Polymers: The Protective Potential of Stents", *Neurosurgery*, 38, (Feb. 1996),339-347.

Yeh, H.-S., et al., "Implantation of intracerebral depth electrodes for monitoring seizures using the Pelorus stereotactic system guided by magnetic resonance imaging", *J. Neurosurg.*, 78, (1993),pp. 138-141.

Zinreich, S. J., et al., "Frameless Sterotaxic Integration of CT Imaging Data: Accuracy and Initial Applications", *Radiology*, 188 (3), (1993),pp. 735-742.

\* cited by examiner

ROBOTIC TRAJECTORY GUIDE

CROSS-REFERENCE TO RELATED APPLICATION

This application claims priority to Provisional Application No. 60/195,662, filed Apr. 7, 2000.

BACKGROUND

1. Field of the Invention

This application relates to medical devices. Specifically, but not by way of limitation, this application relates to inserting medical devices into a patient where the trajectory of the medical device is adjustable from a remote location.

2. Background

When introducing a primary medical device to the inside of a patient, one type of procedure utilizes two additional devices that interact with the primary medical device to aid in precision introduction of the primary medical device. The primary medical device includes an active portion attached to a distal end that may include, but is not limited to: drug delivery capability; a tissue removal instrument such as a laser; an instrument for attaching an electrode; etc. An introducer is a secondary medical device that may be used in a surgical procedure to move a primary medical device along an introduction axis, into or out of the patient. The introducer may be attached to another secondary medical device called a trajectory guide that positions the introducer in the direction of the area to be explored in the patient.

It is important in precision surgical procedures such as neurosurgery that the exact position of the primary medical device is known in precise relation to the position of interest within the body of the patient. For this reason, the relative position of the primary medical device is carefully controlled by secondary medical devices such as introducers and trajectory guides. The trajectory guide fixes the introduction axis to be used by the introducer in three-dimensional space relative to the patient, and the introducer controls the position (depth inside the patient) of the primary medical device along the introduction axis.

To ensure that the secondary medical devices are accurately adjusted relative to the location of interest inside the patient, the trajectory guide must be fixed relative to a patient reference frame. The patient reference frame includes the actual patient, and other objects or devices that the patient is fixed in relation to. The trajectory guide may therefore be fixed directly to the patient in one embodiment. Alternatively, the trajectory guide may be fixed to an intermediate object such as a stereotactic headframe or similar object attached to an operating table, with the patient being fixed to the operating table. For real time imaging, various locating devices may then be attached to the patient reference frame and to the primary medical device reference frame to determine their locations with respect to each other. If retrospective images are being used instead of real time imaging, then the secondary medical devices may be aligned with respect to reference points called fiducials that are located on the patient and that are also visible on the retrospective images.

In real time imaging, the alignment procedure frequently involves the use of a magnetic resonance imaging (MRI) station such as a long bore MR scanner. The MR scanner allows the surgeon to locate the area of interest inside the patient, and to plot a trajectory towards the area of interest. Other types of tissue imaging such as CT and PET are also available.

FIG. 1 shows a ball and socket joint 114 that is used to adjust the manual trajectory guide 100. A base 110 is mounted to a patient using a number of screws 118. Once adjusted, an insertion guide 112 is locked in place with a lockring 116, thus fixing an insertion axis 113 in three dimensional space. When a trajectory guide or other secondary device is used in conjunction with a long bore MR scanner or similar tissue imaging device, adjusting the desired trajectory is frequently a lengthy, iterative process. This is because the surgeon cannot view the patient and adjust the secondary medical devices in "real time." In real time imaging, the patient is inside the MR scanner, and the viewing station for the MR scanner is frequently located at a remote location from the patient. In order to view the MR image of the patient, the surgeon must be outside the long bore MR scanner, looking at the display screen. At the same time, in order to adjust the secondary medical devices, the surgeon must be near the patient, and not in a position to adequately view the display screen. The surgeon typically must remove the patient from the bore of the MR scanner, make an educated adjustment, then return the patient to the bore of the MR scanner, then return to the MR viewing screen to check on how successful the adjustment was. This process can take many iterations.

Although cables or hydraulics could be used to remotely control a secondary medical device, the distance of remote operation is limited. Connecting lines such as cables or hydraulic lines experience friction effects when the connecting lines become sufficiently long. Material compression/tension may also occur over long distances in the cables, housings, hydraulic fluid, etc. Forces such as friction and material compression/tension lead to less accurate adjustment of the secondary device. This effect increases as the remote distance between the patient and the surgeon increases.

Cable communication devices are typically also designed to be adjusted manually, which requires a human operator. In a situation where the surgeon viewing the MR image is several rooms away from the patient, or even miles away from the patient, a second local operator is required to adjust the secondary medical device. As discussed above, this operator must be relatively near the patient due to less accurate adjustments as the operator becomes more remote and the connecting lines become increasingly long.

Another approach that can be used in conjunction with an MR scanner uses a single unit actuator to control the primary medical device. A drawback with this device is that when used inside an MR scanner environment, the entire device must be manufactured to be MR compatible. Devices that are used inside the magnet of an MR imaging scanner cannot be manufactured using magnetic materials due to their interaction with the scanner magnet during operation. Certain non-magnetic metallic materials also interfere with the image being taken, and cannot be used. Even if used outside an MR scanner, the single unit nature of this approach requires the entire device to be sterilized between procedures, or disposed of after each use.

The present inventors have recognized a need for a trajectory guide that can be adjusted without removing the patient from an MR scanner between adjustments. What is also needed is a trajectory guide that can be operated in such a way as to eliminate the need for a second surgical operator in addition to the surgeon viewing the MR scanner image. What is also needed is a trajectory guide that minimizes the negative effects of friction and material compression associated with excessively long cable driven devices. What is also needed is and a trajectory guide that is manufactured to be disposable or convenient to sterilize between procedures.

SUMMARY OF THE INVENTION

An alignment device is shown that includes a base. The base is mounted to a patient reference frame, and may be attached directly to the patient. An insertion guide is attached to the base by an adjustable joint. A local adjustment mechanism is attached to the adjustable joint such that when actuated, the orientation of the insertion guide is adjusted. An actuator is remotely coupled to the local adjustment mechanism, and the actuator can be controlled from a remote location.

In some embodiments, the actuator may be located adjacent to the adjustment devices, in other embodiments, the actuator may be located remote from the adjustment devices. The actuator may be detachable from the adjustment devices and the trajectory guide. The actuator may include electrically powered devices such as an electric motor or a stepper motor.

The alignment device may be part of an alignment system. The system may include an imaging device such as a MRI. The alignment device may be attached to a control module such as a microcomputer. The control module may obtain some of the input information from a first reference device, the reference device being mounted to a primary medical device reference frame. The first reference device may include a number of light emitting diodes (LEDs), or it may include a number of light reflecting point objects. It may also include one or more electrical coils that are influenced by the magnetic field in an MRI. It may also include a linear encoder or a potentiometer.

A second reference device may be included to establish a patient reference frame. The patient reference frame may be compared to the primary device reference frame to establish the location of the primary medical device relative to the patient.

Although specific embodiments have been illustrated and described herein, it will be appreciated by those skilled in the art that any arrangement which is calculated to achieve the same purpose may be substituted for the specific embodiment shown. This application is intended to cover any adaptations of variations of the present invention. It is to be understood that the above description is intended to be illustrative, and not restrictive. The scope of the invention includes any other applications in which the above structures and fabrication methods are used. The scope of the invention should be determined with reference to the appended claims, along with the full scope of equivalents to which such claims are entitled.

DETAILED DESCRIPTION

Figure 1:
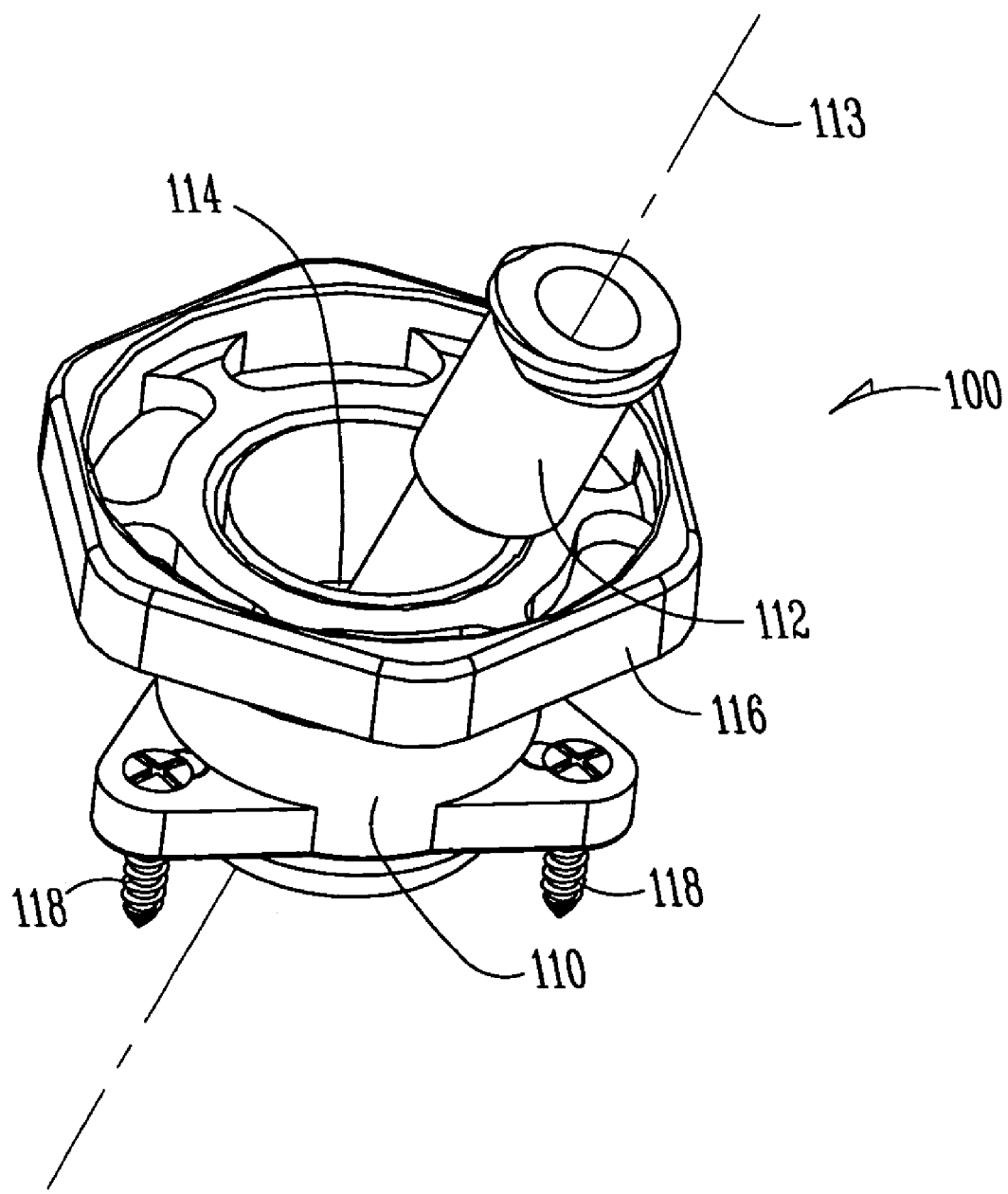
FIG. 1 is a perspective view of a common trajectory guide.
Figure 2:
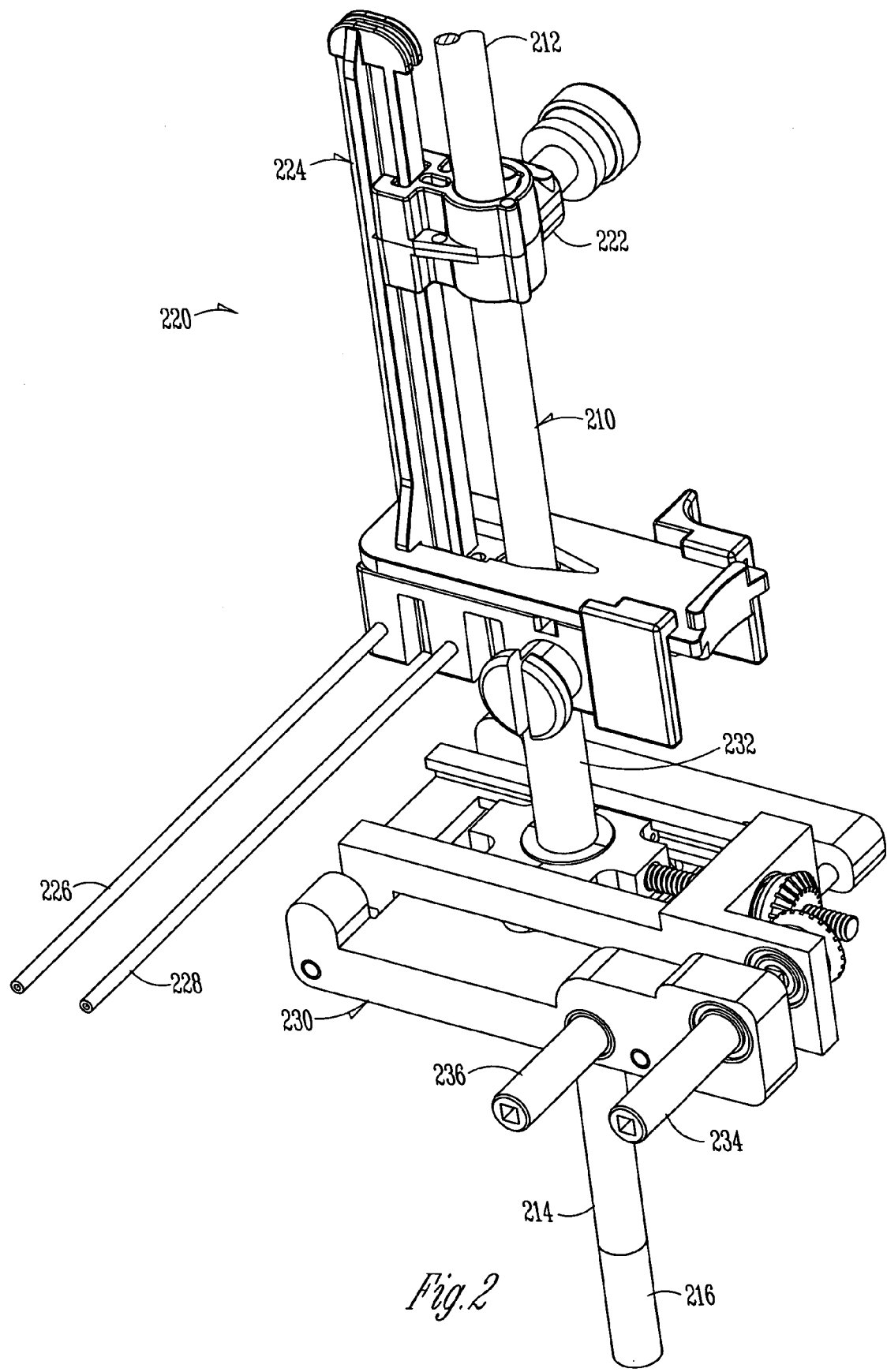
FIG. 2 is a perspective view of an introduction system.

FIG. 2 shows an example introduction system. The system includes a primary medical device 210, an introducer 220 and a trajectory guide 230. An introduction system as described can be used for several procedures that require the introduction of a primary medical device inside a patient. The primary medical device 210 in this embodiment is a catheter that includes a proximal end 212 and a distal end 214, with an active portion 216 attached to the distal end. The active portion may include, but is not limited to: a drug delivery device; a tissue removal instrument such as a laser; an instrument for implanting an electrode; etc.

The introducer 220 shown includes a device holder 222 that moves along a range of motion on a slide 224. The position of the device holder 222 along the range of motion is controlled by a first communication line 226 and a second communication line 228. In this embodiment, the first and second communication lines 226 and 228 are each push-pull cables that may be used to operate the introducer 220 remotely.

The trajectory guide 230 shown includes an insertion guide 232. The position of the insertion guide 232 is controlled by a first interface 234 and a second interface 236. In this embodiment, the first and second interface 234 and 236 are rotating shafts that mechanically adjust an angle of the insertion guide in three dimensional space. The trajectory guides will be discussed in more detail below.

Although the introduction system described could be used to introduce a primary medical device into several areas of a patient, the example discussed involves neurosurgery. The primary medical device in this example is a catheter that is used to probe an internal area of the human brain. The trajectory guide 230 is attached to a patient reference frame. The patient reference frame may include a stereotactic headframe that the trajectory guide is secured to. In this embodiment, the trajectory guide 230 is secured directly to the skull using a number of screws. The introducer 220 is then secured to a proximal end of the insertion guide 232. The primary medical device 210 is inserted through the device holder 222, through the insertion guide 232 and into an opening in the skull. The angle of the insertion guide, relative to the patient reference frame determines an insertion axis. The orientation of this insertion axis is controlled by the trajectory guide, and the position of the active portion 216 of the primary medical device along the insertion axis is controlled by the introducer 220.

Figure 3A:
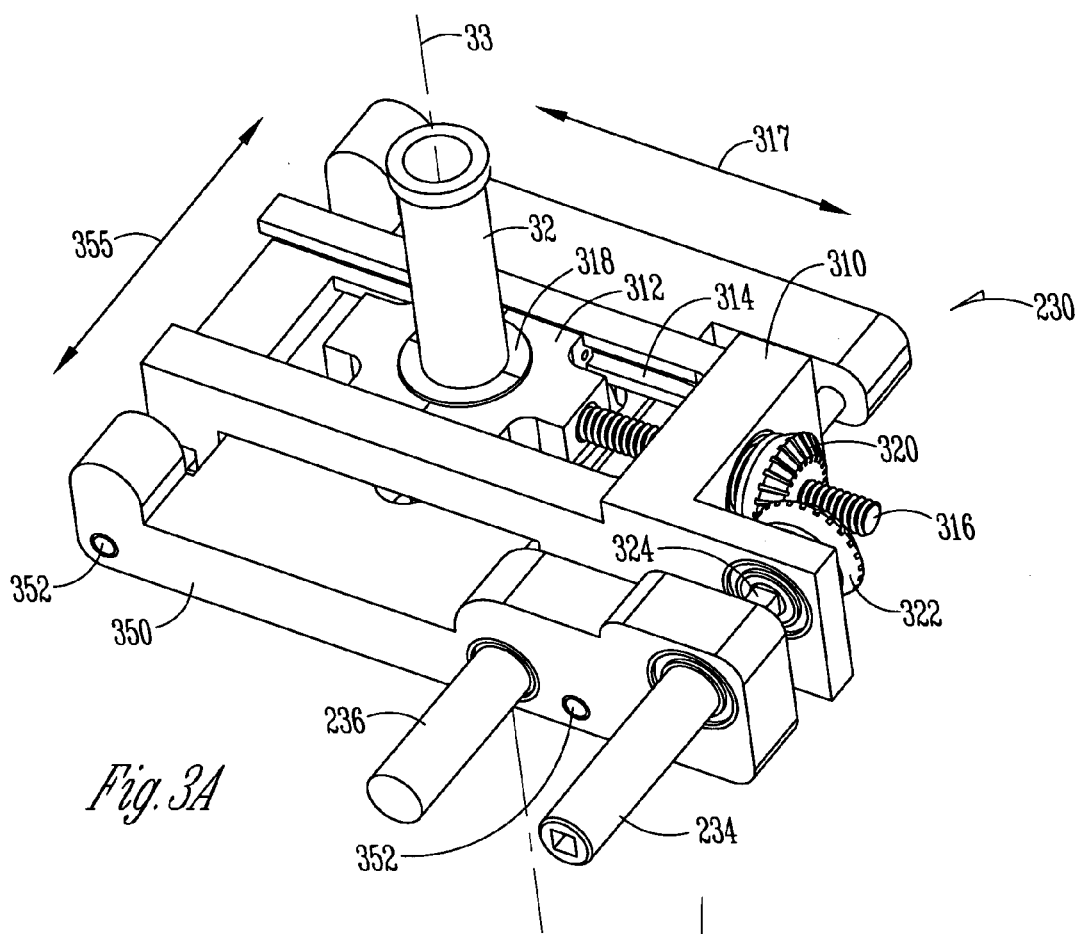
FIG. 3a is a perspective view of a first trajectory guide.
Figure 3B:
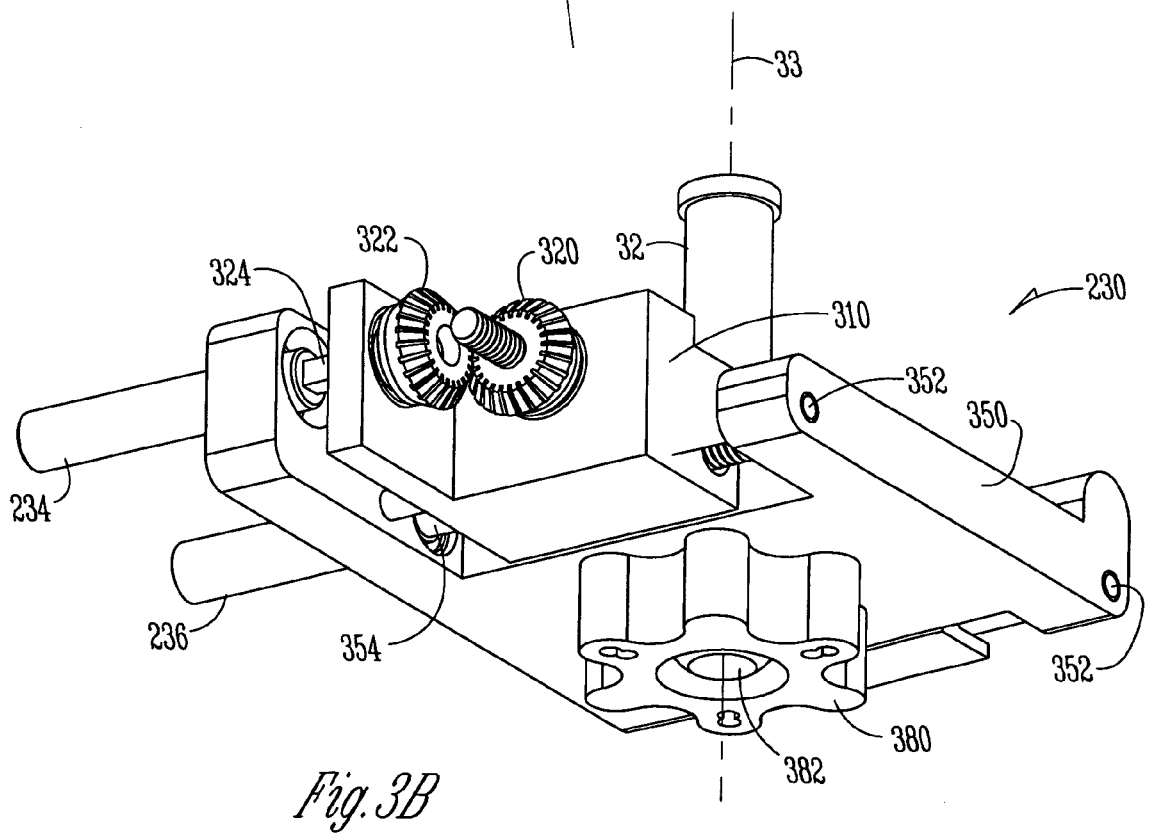
FIG. 3b is a perspective view of one embodiment of a trajectory.

FIGS. 3a and 3b show a first embodiment of the trajectory guide. The trajectory guide 230 includes an insertion guide 32 attached to a base 380 by a ball and socket joint 382. The insertion guide has an insertion axis 33 along which the primary medical is guided. Orientation of the insertion guide, and hence the insertion axis, is accomplished with a pair of adjustment devices. It should be noted that although in this embodiment, a ball and socket joint is used with a pair of adjustment devices, that any of a number of joints could be used and any number of adjustment devices could be used without departing from the scope of the invention. Additionally, while this embodiment describes rotational adjustments in angle of the insertion axis, other embodiments include adjustments such as translational motion of the insertion axis within three dimensional space.

A first adjustment device includes a first slide 310. The first slide 310 includes a block 312 that rides along a pair of rails 314. The block is attached to a first threaded member 316. When the first threaded member 316 is actuated, the block 312 is moved along the rails 314 in a first degree of freedom shown by arrows 317. Block 312, includes a collar 318 that encompasses the insertion guide 32. The collar 318 is designed as a ball and socket joint with the block 312 so that various angles of the insertion guide 32 can be accommodated.

A second adjustment device includes a second slide 350. The second slide 350 includes a pair of rails 352 upon which the entire first slide 310 moves. The first slide 310 has a second threaded member 354 attached to it, such that when rotated, the first slide 310 moves along the rails 352 in a second degree of freedom shown by arrows 355. The collar 318 of the first slide 310 also serves to accommodate angles of adjustment made with the second slide 350.

Further attached to the first threaded member 316 is a first beveled gear 320 that meshes with a second bevel gear 322. The second bevel gear 322 is attached to a shaft 324 that in turn is attached to the first interface 234. The second interface 236 is connected to the second threaded member 354.

In operation, rotation of the first interface 234 drives the shaft 324 and rotates the second bevel gear 322. The second bevel gear 322 engages the first bevel gear 320 causing the first threaded member 316 to thread through the first bevel gear 320. Motion of the first threaded 316 member through the first bevel gear 320 in turn moves the block 312 and changes the angle of the insertion axis 33 in the direction of arrows 317. Rotation of the second interface 236 directly drives the second threaded member 354 which moves the first slide 310. Rotation of the second interface 236 therefore adjusts the angle of the insertion axis 33 in the direction of arrows 355. By adjusting a combination of the first and second slides 310 and 350, any of a number of orientations of the insertion axis 33 can be obtained in three dimensional space.

Because of the local positioning of adjustment devices such as the first and second slide 310 and 350, precise adjustments to the angle of the insertion axis 33 can be made with negligible effects from friction, material compression/tension, or hysteresis. In contrast, adjustment devices that are remotely coupled to the insertion guide are subject to less alignment accuracy due to friction in cables, stretching of cables, or hysteresis of the cable once it has been stretched for example.

Figure 4:
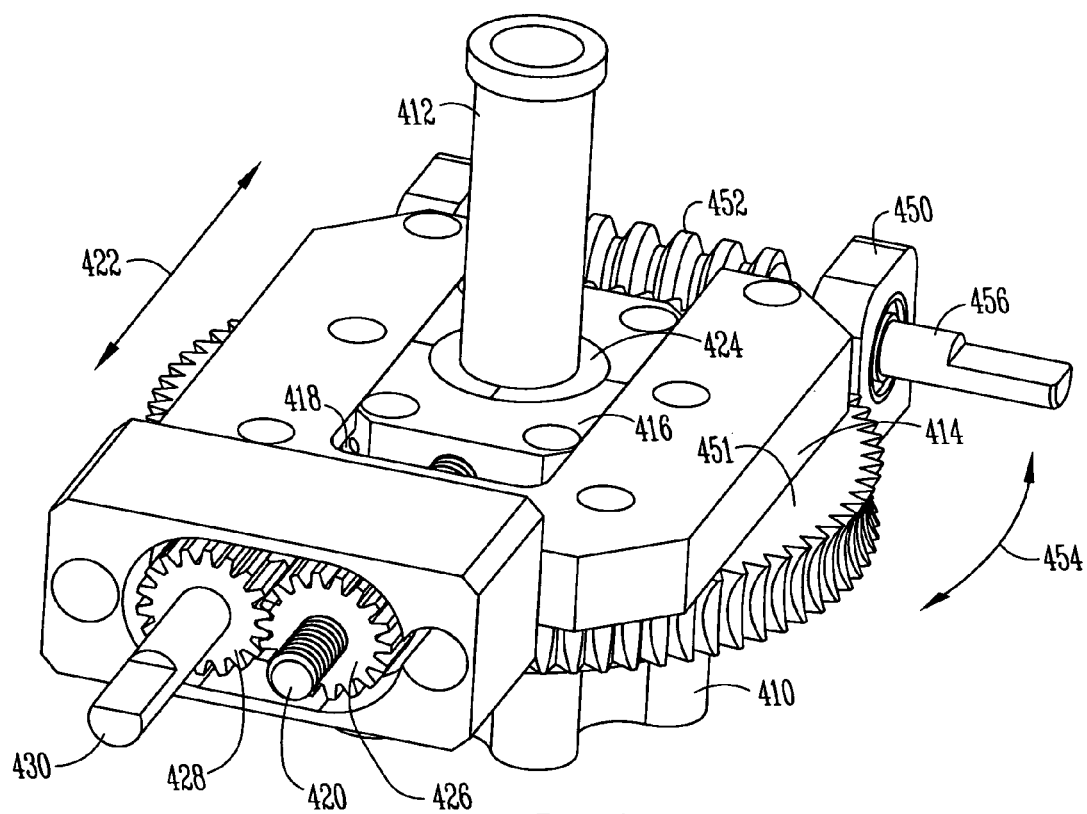
FIG. 4 is a perspective view of another embodiment of a trajectory guide.

A second embodiment of a trajectory guide is shown in FIG. 4. An insertion guide 412 is shown attached to a base 410 by a ball and socket joint similar to the first embodiment. A slide 414 is shown, the slide including a block 416, the block 416 sliding along rails 418. A threaded member 420 is attached to the block 416, such that when the threaded member is actuated, the block moves in a first degree of freedom indicated by arrows 422. Additionally, as in the first embodiment, the block 416 is fitted with a collar 424 that allows adjustment of the insertion guide 412 through a ball and socket joint. A first gear 426 is coupled to the threaded member 420. The first gear 426 is fixed spatially on the slide 414, but allowed to rotate. A second gear 428 engages the first gear, and the second gear is attached to a first interface 430.

A worm drive 450 is also shown in FIG. 4. The worm drive includes a drive gear 451 that is attached to the slide 414. The drive gear 451 is engaged by a worm gear 452 that is in turn coupled to a second interface 456. When the worm gear 452 is actuated, the insertion guide is adjusted in a second degree of freedom as indicated by arrows 454.

In operation, rotation of the first interface 430 drives rotation of the second gear 428 which in turn engages the first gear 426. The first gear is fixed spatially, but is free to rotate. In rotation, the first gear 426 threads the threaded member 420 back and forth in the directions according to arrows 422. In turn, this adjusts the orientation of the insertion guide 412 in the range of motion indicated by arrows 422. Rotation of the second interface 456 drives rotation of the worm gear 452, which in turn engages the drive gear 451. Because the drive gear 451 is attached to the slide 414, which is attached to the insertion guide 412, rotation of the drive gear 451 adjusts the orientation of the insertion guide 412 according to arrows 454. By adjusting a combination of the slide 414 and the worm drive 450, any of a number of orientations of the insertion guide 412 can be obtained in three dimensional space.

Similar to the first embodiment of the trajectory guide, the local positioning of adjustment devices such as the slide 414 and the worm drive 450, allows precise adjustments to the angle of the insertion guide 412, can be made with negligible effects from friction, material compression/tension, or hysteresis.

Figure 5:
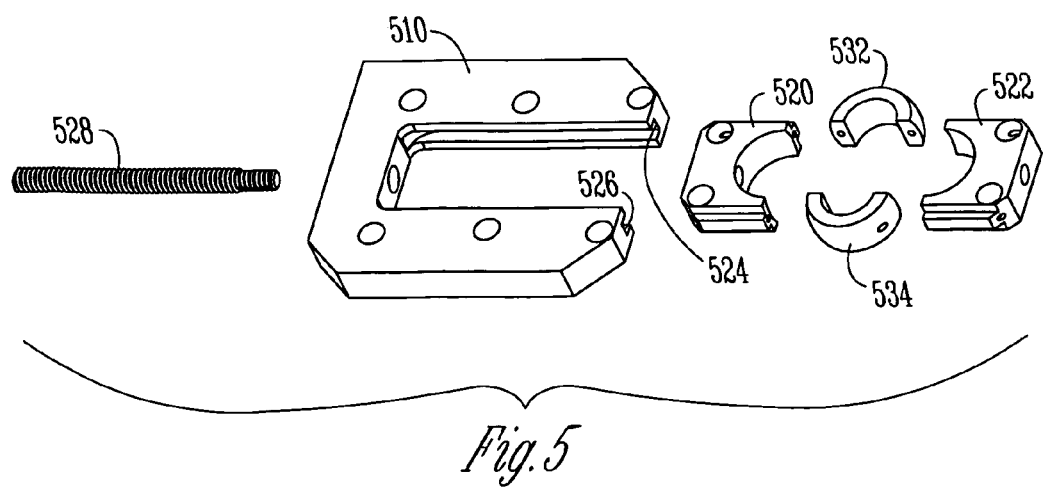
FIG. 5 is an exploded view of a linear slide adjustment device.

FIG. 5 shows the slide 414 from FIG. 4 in more detail. A slide body 510 is shown with a first rail 524 and a second rail 526. A threaded member 528 is inserted through the slide body 510 and attached to a first block part 520. A first collar part 532 is combined with a second collar part 534 to form the collar 424 from FIG. 4. A second block part 522 then is combined with the first block part 520 around the first and second collar parts 532 and 534. The combination of the block parts and the collar parts forms a ball and socket joint which allows the insertion guide 412 to move in various angles. In this embodiment, the threaded member 528 is not itself rotated, and motion is accomplished by rotation of the first gear 426. One skilled in the art will recognize that the threaded member 528 can also be threaded into the slide body 510 and rotated to accomplish motion of the threaded member 528.

Although specific mechanical adjustment devices have been shown in these embodiments, one skilled in the art will recognize that other adjustment devices can be used as locally mounted adjustment devices without departing from the scope of the invention.

Figure 6A:
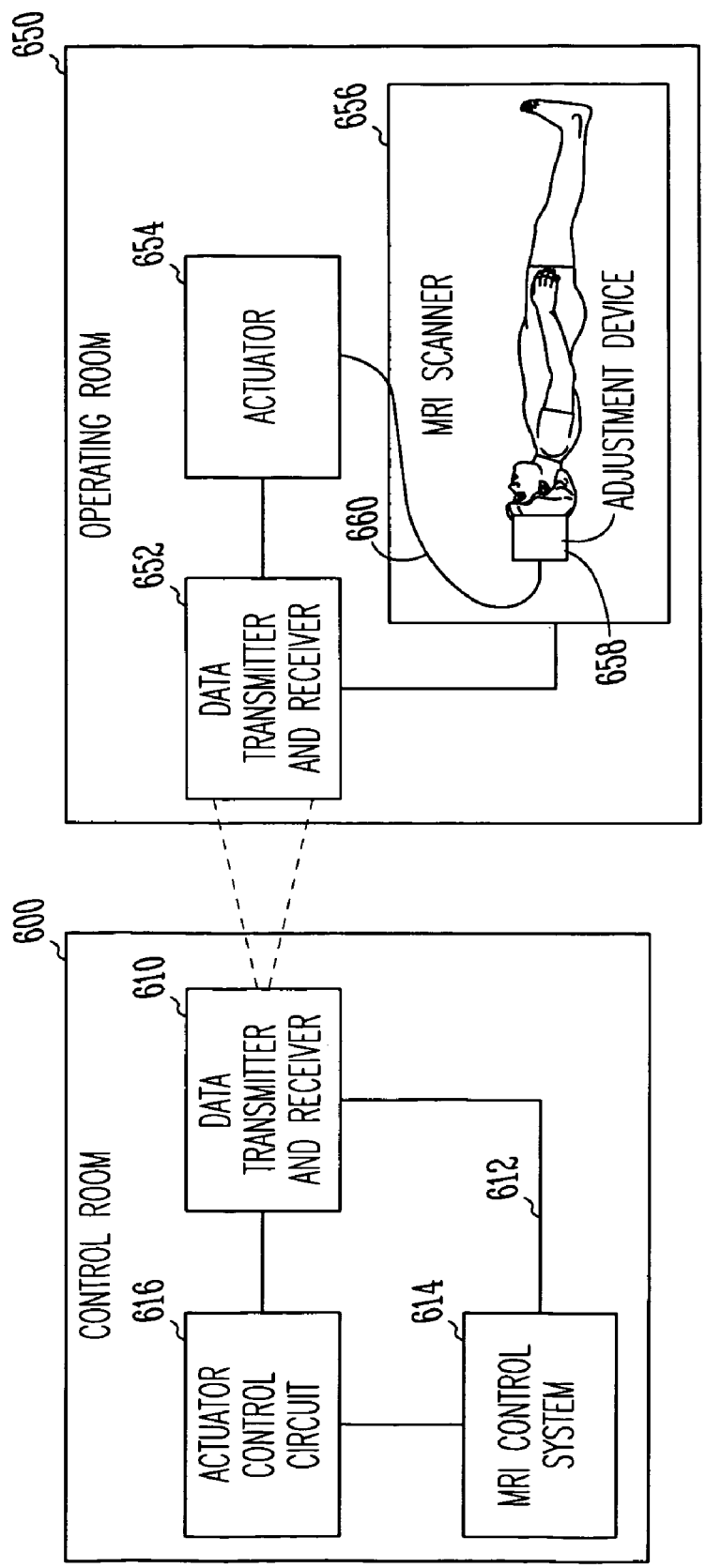
FIG. 6a is a schematic diagram of one embodiment of an introduction system.
Figure 6B:
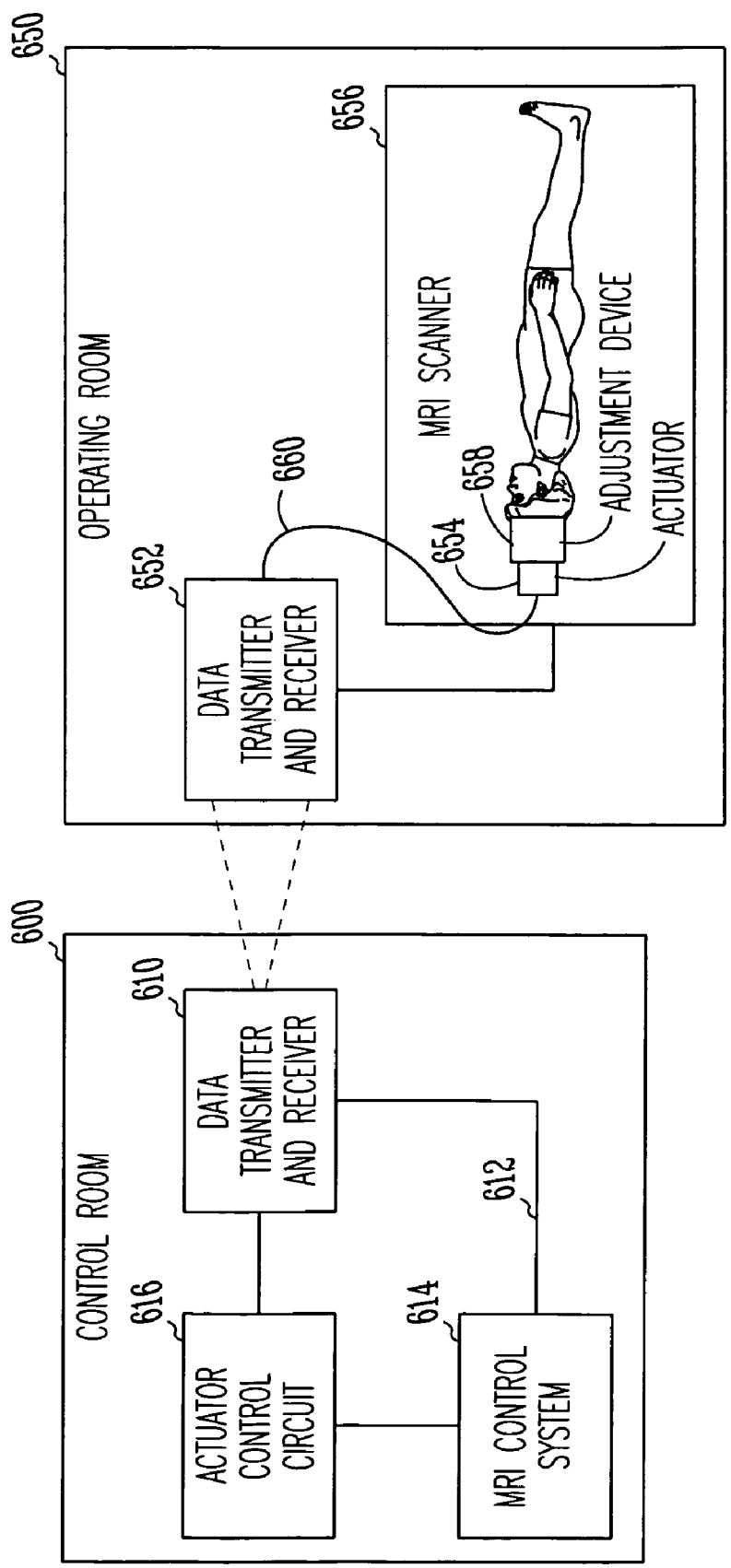
FIG. 6b is a schematic diagram of another embodiment of an introduction system.

FIGS. 6a and 6b show configurations of an introduction system according to the invention. Two separate rooms are shown, a control room 600 where a tissue imaging device such as an MRI is controlled from, and an operating room 650 where a patient is located and where the active tissue imaging device such as an MRI magnet (scanner) is located. Other types of tissue imaging such as CT and PET are also possible. The MRI control system 614 is shown coupled to a first data transmitter/receiver 610. A control module such as a microcomputer 616 is also located in the control room 600. The control module 616 in one embodiment is integrated within the control system 614. The devices in the rooms shown in FIGS. 6a and 6b are connected by communication lines 612. Such lines are typically electrically conducting wire, but could be other types of communication lines such as fiber optic lines, or the communication could be wireless without departing from the scope of the invention.

In FIG. 6a, the operating room 650 shows an MRI scanner 650 with a patient located inside the scanner 650. A second data transmitter/receiver 652 is shown in communication with the first data transmitter/receiver 610. An actuator 654 is shown outside the MRI scanner 656, the actuator being in communication with the second data transmitter/receiver 652, and in communication with an adjustment device 658. In this embodiment, the actuator 654 is in communication with the adjustment device 658 through a mechanical communication line 660. In this embodiment, the mechanical communication lines 660 are rotary cables. The adjustment device 658 is a part of the trajectory guide as discussed above, which is in turn attached to the patient.

In operation, the surgeon is located in the control room 600, and is viewing the scanned image of the patient in the operating room 650. The surgeon is also able to access the actuator control circuit 616. In real time, the surgeon is able to remotely view the patient, and remotely make adjustments to the insertion axis of the trajectory guide. A signal for an adjustment is sent from the first data transmitter/receiver 610 to the second data transmitter/receiver 652. The received signal is sent to the actuator 654 that in turn actuates the adjustment device 658.

The actuator 654 in this embodiment might include a electrical motor or another electrical actuator. The actuator 654 provides the force necessary to actuate the adjustment device, which as shown in this embodiment, mainly translates the force provided by the actuator into the desired motion of the insertion guide. An advantage of this configuration is that because the actuator is not located within the MRI scanner, it does not need to be manufactured to be MR compatible. Actuators such as electric motors are difficult and expensive to design is such a way as to be MR compatible. Additionally, the trajectory guide, with its associated adjustment device 658 can be designed to be easily detachable. In this way, the more expensive actuator 654 can be reused, potentially without intensive sterilization, and the trajectory device can be more easily sterilized, or alternatively, disposed of after each procedure.

FIG. 6b shows a similar arrangement to FIG. 6a, with the exception that the actuator from FIG. 6a is now located adjacent to the adjustment device. In this arrangement, the mechanical communication lines 660 are minimized or eliminated, which reduces frictional losses and material compression/tension losses. The actuator 654 in this configuration is MR compatible. The actuator in this configuration is still detachable from the adjustment device. In this way, the trajectory guide may be manufactured to be disposable, while the actuator is reused for each procedure.

The configurations shown in FIG. 6a and 6b both have the advantage of trajectory guides that are controllable from outside the MR scanner 656. Not only are they controllable from outside the MR scanner, they eliminate the need for a second surgical operator to make the adjustments to the trajectory guide. Also, when electrical signals or digital signals are sent to the actuators, there is a greater accuracy over long distances than would be possible with a mechanical signal. Mechanical signals are susceptible to the friction losses and material compressions/tensions that have been discussed. Electrical signals degrade very little, even over long distances. With the configurations in FIGS. 6a and 6b, not only is it possible to make very accurate adjustments from another room such as the control room 600, it is also possible to make adjustments from very remote locations through communications lines such as telephone lines, or through use of the internet.

Figure 7A:
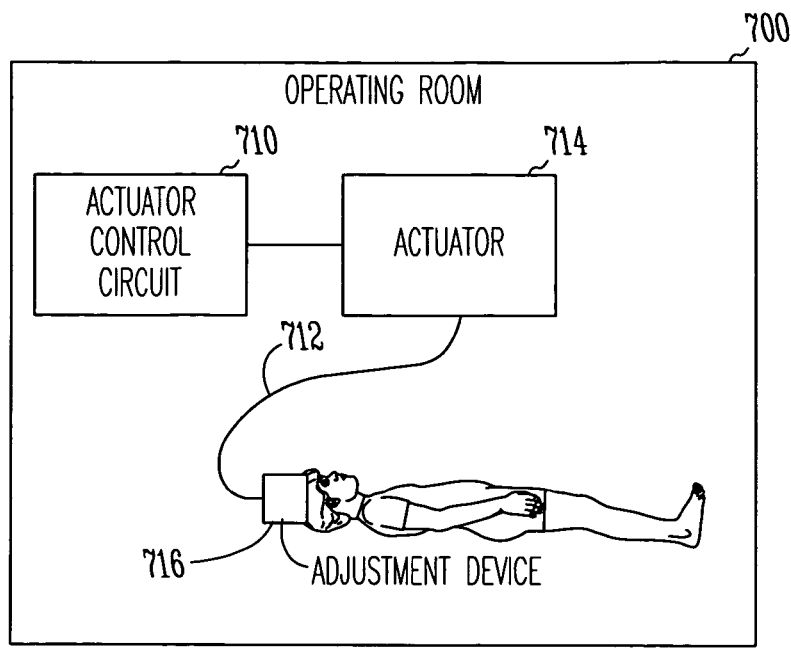
FIG. 7a is a schematic diagram of another embodiment of an introduction system.
Figure 7B:
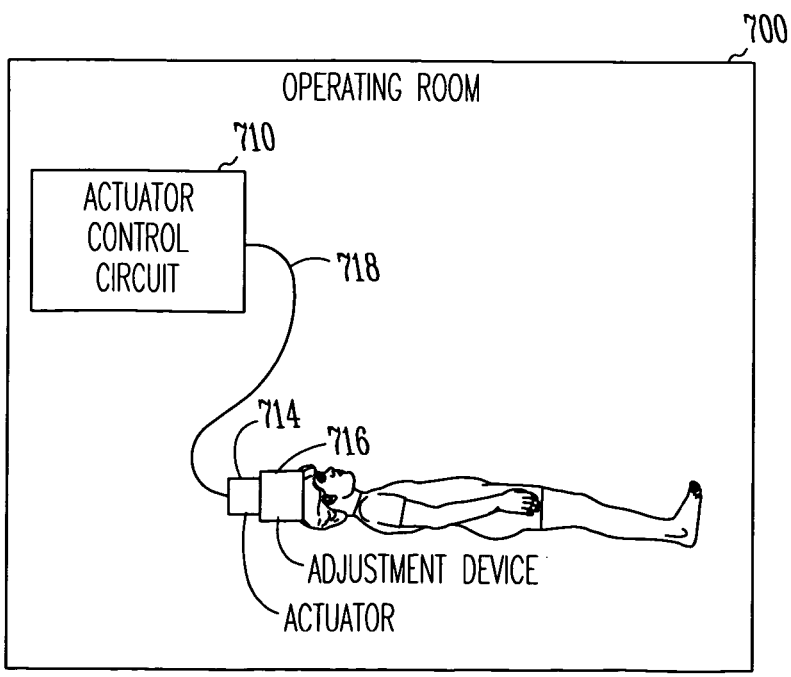
FIG. 7b is a schematic diagram of another embodiment of an introduction system.

FIGS. 7a and 7b show the use of the introduction system without the aid of real time tissue imaging. Using previously obtained images, the trajectory guide can be registered with fiducials located on the patient, the fiducials also being visible in the previously obtained images.

The operating room 700 in FIGS. 7a and 7b includes an actuator control circuit 710 such as a microcomputer. An adjustment device 716 from a trajectory guide is again attached to the patient. The introduction system, may be configured such that the actuator 714 is remote from the adjustment device 716 and connected to the adjustment device by mechanical communication lines 712. In this configuration, the weight of the devices directly attached to the patient is minimal, which reduces the need for external device support.

Alternatively in FIG. 7b, the actuator 716 is attached adjacent to the adjustment device 714, and utilizes optical or electrical communication lines 718. In this configuration, the mechanical communication lines 712 are minimized or eliminated, which reduces frictional losses and material compression/tension losses. The actuator in this configuration is still detachable from the adjustment device, and the adjustment device may be manufactured to be disposable, while the actuator is reused for each procedure.

Figure 8:
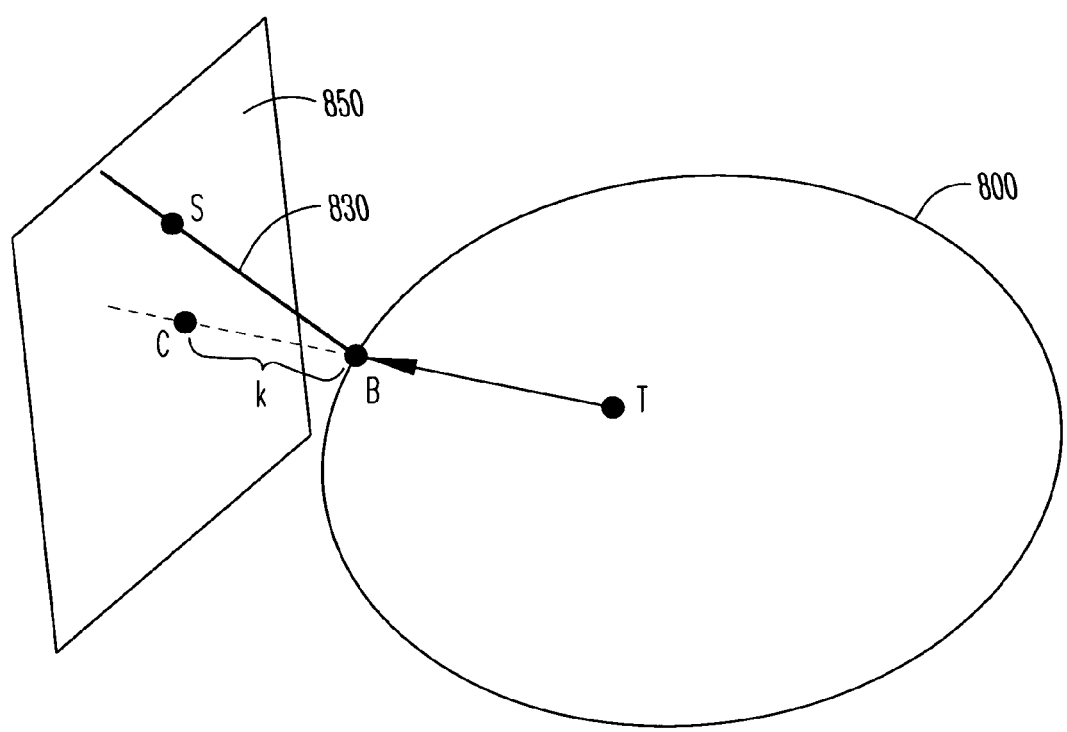
FIG. 8 is a perspective diagram of vectors used in operation of the trajectory guide.

FIG. 8 shows one embodiment of a vector schematic diagram used by the microcomputer when actuating the adjustment devices to align the insertion guide. The skull 800 is shown with a target point T inside the skull. The entry point at the outside of the skull is indicated as point B. The insertion axis 830 of the insertion guide is shown intersecting point B. In this embodiment, the angle used to image the patient is shown by image plane 850. The image plane 850 in this embodiment has a center point C. The image in this embodiment is adjusted so that the target point T is at the center of the image C. The insertion axis 830 is then adjusted so that it is collinear with the line TB using a process flow according to FIG. 9. Although it is advantageous in this embodiment to utilize line TB, another embodiment could use only point T, and determine when insertion axis 830 intersects point T.

Figure 9:
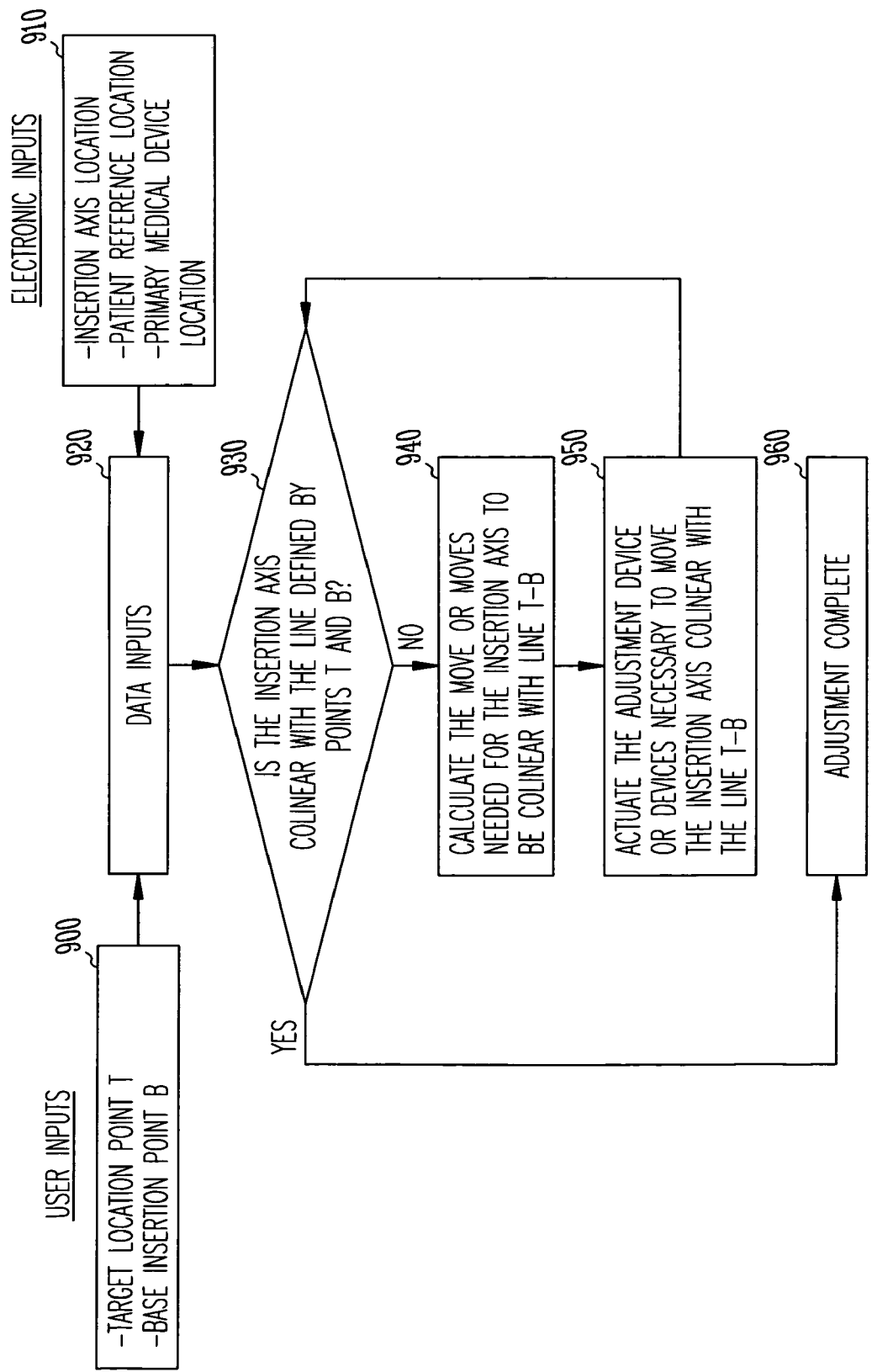
FIG. 9 is a block diagram outlining operation of the trajectory guide.

FIG. 9 shows user inputs 900, such as point T and B as indicated in FIG. 8. Although point B is shown as a user input, this point could also be derived from outside electronic inputs. Electronic inputs 910 in this embodiment include the orientation of the insertion axis, the relative location of the patient, and the location of the primary medical device along the insertion axis.

Both user inputs 900 and electronic inputs 910 are used as data inputs 920 to calculate the insertion axis 830 and the line TB from FIG. 8. In stage 930, the software of the microcomputer determines whether or not the insertion axis 830 is collinear with the line TB. If the they are collinear, then the process is finished at stage 960. If they are not collinear, in stage 940, the software calculates the direction and magnitude of moves necessary to make the insertion axis 830 collinear with line TB. Then in stage 950, the microcomputer sends signals to the actuator or actuators to execute the calculated moves from stage 940. After stage 950, the process flow is returned to stage 930 where the software again checks whether or not the insertion axis is collinear with line TB.

In one embodiment described above, the configuration is a closed loop system. In the closed loop system, once a target location has been input into the control module, the control circuit calculates and adjusts the trajectory without further input from the user. The closed loop system is constantly evaluating the condition of the system through a feedback loop. Feedback inputs include the orientation/position of the primary and secondary medical devices and, in real time imaging, the target location. A closed loop system as such, eliminates the need for several manual operator iterative adjustments to the trajectory guide or other secondary devices. A closed loop system is also capable of compensating for any remaining frictional or compression/tension loss effects in the system. One closed loop configuration makes the necessary adjustments to align the trajectory guide all at one speed. Another closed loop configuration adjusts the speed of the adjustments by slowing down the adjustment speed as the exact alignment/position is near. Another configuration calculates the moves necessary for alignment, and actuates the adjustment devices incrementally, waiting for operator input between moves.

Although the closed loop system described focuses on alignment of a trajectory guide, other secondary medical devices may be controlled using the closed loop system, such as an introducer. In this manner, all orientations and positions of a primary medical device in a procedure are controlled through the control module.

One skilled in the art will recognize that although a microcomputer is described, any of a number of varieties of control modules could be used. Additionally, the software or algorithm used could be configured in many different embodiments to achieve the same goal of aligning the insertion axis 830 with the line TB.

Electronic inputs 910 from FIG. 9 can be determined by several methods. Software included with the microcomputer may recognize the primary and secondary medical devices on the image and, through an algorithm, determine their location.

Another embodiment includes a first reference device located on the reference frame of the primary medical device. The reference device includes a number of light emitting diodes (LEDs) that are detectable with the imaging device. If three LEDs are used, the three points would determine the orientation of the primary medical device in three dimensions. Alternatively, the three points could be light reflecting points, where a light source is directed towards the light reflecting points and the reflected light is detected to determine an orientation of the primary medical device in three dimensional space.

Another example attaches one or more electrical coils to the primary medical device reference frame. In an MRI environment, an electrical coil has a varying electrical response depending on its orientation inside the MR scanner. The variations in electrical response can be used to indicate an orientation and/or location of the primary medical device in three dimensional space.

Another example attaches an encoder or a potentiometer to the primary medical device reference frame. The use of an encoder or potentiometer locates the primary medical device along an axis, the orientation of which may have been determined by the number of LEDs, reflecting points, or electrical coils described above.

Additionally, a second reference device could be located in the patient reference frame. If two reference devices are used (one attached to the primary medical device reference frame, the other attached to the patient reference frame) then the first and second reference devices can be used to determine a location of the primary medical device relative to the patient.

Although specific embodiments have been illustrated and described herein, it will be appreciated by those skilled in the art that any arrangement which is calculated to achieve the same purpose may be substituted for the specific embodiment shown. This application is intended to cover any adaptations of variations of the present invention. It is to be understood that the above description is intended to be illustrative, and not restrictive. The scope of the invention includes any other applications in which the above structures and fabrication methods are used. The scope of the invention should be determined with reference to the appended claims, along with the full scope of equivalents to which such claims are entitled.

The invention claimed is:

1. An alignment system for an imaging device comprising:
   an alignment device comprising:
      a base, the base having an affixation deice to mount on a patient surface;
      an insertion guide, having an opening therein and an insertion axis through the opening;
      an adjustable joint attached to a distal end of the insertion guide, and coupled to the base;
      an MR compatible local device including:
         a slide body movably coupled to the base;
         a block slidably attached to the slide body;
         a collar engaged to the insertion guide and movably retained by the block, the collar and block forming a ball and socket joint between the block and the insertion guide; and
         a threaded adjuster coupled to the block, the threaded adjuster configured to cause linear motion of the collar with respect to the slide;
      an actuator detachably coupled to the local adjustment device, wherein the actuator is spaced apart from the local adjustment device to enable location of the actuator outside an imaging region of the imaging device while the local adjustment device is within the imaging region of the imaging device; and
   a control module in remote communication with the actuator and in communication with the imaging device, the control module aligning the insertion axis with the target location.

2. The alignment system of claim 1, wherein the control module includes microcomputer.

3. The alignment system of claim 1, wherein the imaging device includes a magnetic resonance imaging (MRI) device.

4. The alignment system of claim 1, further including a first reference device coupled to the insertion guide, the first reference device being capable of locating the insertion axis in three dimensional space relative to a patient.

5. The alignment system of claim 4, further including a second reference device coupled to a patient reference frame, the second reference device being capable of locating the patient relative to the first reference device.

6. The alignment system of claim 4, wherein the first reference device includes a conducting coil capable of locating the insertion axis in three dimensional space relative to the patient.

7. The alignment system of claim 4, wherein the first reference device includes a number of LED devices capable of locating the insertion axis in three dimensional space relative to the patient.

8. The alignment system of claim 4, wherein the first reference device includes a number of infra red (IR) reflecting devices capable of locating the insertion axis in three dimensional space relative to the patient.

9. The alignment system of claim 4, wherein the first reference device includes a potentiometer capable of locating a primary medical device along the insertion axis.

10. The alignment system of claim 4, wherein the alignment system is a closed loop system.

11. The alignment system of claim 1, wherein the adjustable joint includes a ball and socket joint.

12. A method of aligning a medical device comprising:
coupling a base to a patient reference frame;
attaching an insertion guide to the base using an adjustable joint, the insertion guide having an insertion axis, and the adjustable joint having a range of motion;
attaching a local adjustment device to the adjustable joint, the local adjustment device including a slide body movably coupled to the base, a block slidably attached to the slide body, and a collar angaged to the insertion guide and movably retained by the block, the collar and block forming a ball and socket joint between the block and the insertion guide;
coupling an actuator to the local adjustment device; wherein coupling the actuator to the local adjustment device includes remotely coupling the actuator to the local adjustment device
remotely actuating the actuator to adjust alignment of the insertion axis within the range of motion, the actuator configured to cause at least one of motion of the slide body with respect to the base and linear motion of the block with respect to the body, the motion of the slide body with respect to the base being one of linear motion and rotatable motion; and
detaching the actuator from the local adjustment device upon completion of a procedure.

13. The method of claim 12, wherein coupling a base includes attaching a base directly to the skull of a patient.

14. The method of claim 12, wherein actuating the actuator includes engaging a rotary motor, the rotary motor being coupled to the local adjustment device by a rotating cable drive.

15. The method of claim 14, further including coupling the actuator to a remote control module, the remote control module being capable of adjusting the insertion axis by remotely actuating the actuator.

16. The method of claim 15, further including:
imaging a patient with a tissue imaging device;
inputting a target location to the control module; and
computing an adjustment with the control module and aligning the insertion axis with the target location through actuation of the actuator.

17. The method of claim 16, wherein computing an adjustment with the control module and aligning the insertion axis includes computing an adjustment with the control module and aligning the insertion axis using a closed loop system.

* * * * *

UNITED STATES PATENT AND TRADEMARK OFFICE
CERTIFICATE OF CORRECTION

PATENT NO. : 7,366,561 B2
APPLICATION NO. : 09/825786
DATED : April 29, 2008
INVENTOR(S) : Mills et al.

It is certified that error appears in the above-identified patent and that said Letters Patent is hereby corrected as shown below:

Col. 10, Line 18: "affixation deice" should read --affixation device--

Col. 10, Line 24: "local device" should read --local adjustment device--

Col. 11, Line 11: "base to a patient reference frame;" should read --base directly to a patient surface;--

Col. 11, Line 15: "attaching a local" should read --attaching a multi-axis local--

Col. 12, Line 1: "respect to the body," should read --respect to the slide body,--

Signed and Sealed this

Second Day of September, 2008

JON W. DUDAS
*Director of the United States Patent and Trademark Office*